United States Patent [19]

Antrim et al.

[11] Patent Number: 4,961,939

[45] Date of Patent: Oct. 9, 1990

[54] DEODORIZED WATER-IN-OIL EMULSION CONTAINING FISH OIL

[75] Inventors: Richard L. Antrim; James B. Taylor, both of Sparta, N.J.

[73] Assignee: Nabisco Brands, Inc., East Hanover, N.J.

[21] Appl. No.: 360,630

[22] Filed: Jun. 2, 1989

[51] Int. Cl.$^5$ .................. A23D 7/00; A23C 15/00

[52] U.S. Cl. ...................................... 426/61; 426/602; 426/603; 426/608; 426/654; 514/355

[58] Field of Search .................. 426/61, 602–604, 426/608, 7, 56, 643, 33, 654; 514/355

[56] References Cited

U.S. PATENT DOCUMENTS

| | | | |
|---|---|---|---|
| 3,249,442 | 5/1966 | Keyes et al. | 99/18 |
| 3,562,301 | 2/1971 | Fryer et al. | |
| 4,232,044 | 11/1980 | Chiba et al. | 426/44 |
| 4,775,749 | 10/1988 | Hijiya et al. | |

FOREIGN PATENT DOCUMENTS

| | | |
|---|---|---|
| 53-137206 | 11/1978 | Japan . |
| 54-114507 | 9/1979 | Japan . |
| 57-096095 | 6/1982 | Japan . |
| 58-080393 | 5/1983 | Japan . |
| 58-089186 | 5/1983 | Japan . |
| 58-094386 | 6/1983 | Japan . |
| 58-165796 | 9/1983 | Japan . |
| 58-192813 | 11/1983 | Japan . |
| 59-21609 | 2/1984 | Japan . |
| 59-113099 | 6/1984 | Japan . |
| 59-172596 | 9/1984 | Japan . |
| 60-87205 | 5/1985 | Japan . |
| 60-102168 | 6/1985 | Japan . |
| 60-207560 | 10/1985 | Japan . |

OTHER PUBLICATIONS

Enzymatic Improvement of Food Flavor I., N. Takahashi et al., Agric. Biol. Chem., 43 (9), pp. 1873–1882, 1979.
Enzymatic Improvement of Food Flavor II., H. Chiba et al., Agric. Biol. Chem., 43 (9), pp. 1883–1889, 1979.
Enzymatic Improvement of Food Flavor III., H. Chiba et al., Agric. Biol. Chem., 43 (9), pp. 1891–1897, 1979.
Enzymatic Improvement of Food Flavor IV., N. Takahashi et al., Agric. Biol. Chem., 43 (12), pp. 2557–2561, 1979.
Changes of Aldehyde Levels In Defatted Soybeam Extract, R. Sasaki et al., J. Food Science, 47, pp. 31–35, 1981.

*Primary Examiner*—Marianne Cintins

[57] ABSTRACT

The present invention is directed to water-in-oil and oil-in-water emulsions containing fish oil which are stabilized by enzyme systems which prevents or retards against the deleterious formation of malodorous alcohols and aldehydes thereby eliminating the undesired odor and off-flavor associated with the formation of these organic products. The enzyme system contemplated by the present invention include compositions of (a) aldehyde dehydrogenase plus alcohol dehydrogenase plus nicotinamide adenine dinucleotide (NAD); (b) aldehyde oxidase plus alcohol oxidase plus catalase; and (c) xanthine oxidase plus alcohol oxidase plus catalase.

11 Claims, No Drawings

DEODORIZED WATER-IN-OIL EMULSION CONTAINING FISH OIL

BACKGROUND OF THE INVENTION

The present invention relates to water-in-oil and oil-in-water emulsions which contain significant amounts of fish oil in the oil phase thereof and which are stabilized against the formation of malodorous alcohols and aldehydes therein during the shelf life thereof by the use therein of certain enzyme based stabilization systems.

DESCRIPTION OF THE PRIOR ART

For economic and health reasons, it is desirable to replace some or all of the vegetable oils that have been used heretofore in ingestible water-in-oil and oil-in-water emulsions with less expensive and more healthful fish oils. These fish oils, however, may contain, and are prone to produce during the shelf life thereof, malodorous aldehydes or alcohols. These malodorous compounds, even at relatively low concentrations, of the order of about 0.005 to 0.7 parts per million (ppm), emit odors which are readily detectable by the average consumer of the emulsions and are organoleptically undesirable.

These aldehydes and alcohols are formed in situ by oxidation of the fish oils. However, the degree of oxidation leading to the formation of these malodorous aldehydes and alcohols is substantially less than that required to cause rancidity.

Several prior art publications disclose the use of certain enzyme based systems to remove aldehydes and alcohols, as sources of off-flavor, from soybean based protein materials. See for example in this regard U.S. Pat. No. 4,232,044 (J. Chiba et al.)

Agric. Biol. Chem., 43 (9), pages 1873-1882, 1979 N. Takahashi et al.

Agric. Biol. Chem., 43 (9), pages 1883-1889, 1979, H. Chiba et al.

Agric. Biol. Chem., 43 (9), pages 1891-1897, 1979, H. Chiba et al.

Agric. Biol. Chem., 43 (12), pages 2557-2561, 1979, N. Takahashi et al.

J. Food Sci., 47, pages 31-35, 1982, R. Sasaki et al.

This technology essentially requires the removal of the offending alcohol or aldehyde from the soybean protein after the malodorous compounds are formed and prior to the commercialization of the soybean based products.

Prior to the present invention, the prior art has not provided an enzyme based stabilization system designed to protect fish oil containing emulsions from either forming objectionable levels of malodorous aldehydes and alcohols therein during the normal shelf life of such emulsions or by readily removing the malodorous compounds in situ during the commercial shelf life of the emulsion.

OBJECTS OF THE PRESENT INVENTION

An object of the present invention is to render water-in-oil and oil-in-water emulsions containing fish oil stable during storage and use relative to the formation therein of malodorous aldehydes and alcohols.

DESCRIPTION OF THE PREFERRED EMBODIMENT

The Emulsions

The emulsions which are the subject of the present invention are water-in-oil and oil-in-water emulsions which are formulated with food components. In formulating these products according to the present invention, some or all of the vegetable or animal derived oils previously used by those in the art of formulating such products are replaced by fish oil.

If the fish oil is a solid at ambient temperatures (i.e. about 25° C.), it may be heated to liquify it prior to its use in forming the desired emulsions.

The food type emulsions of the present invention would include oil-in-water type emulsions such as mayonnaise and salad dressing and water-in-oil type emulsions such as margarine, butter and buttery margarine.

The term "buttery margarine" means a margarine product made with at least 80% non-butter fat, and which has added thereto enough artificial or natural butter flavor to impart a discernible butter flavor taste thereto.

The term "butter" as used herein means a product commonly made only with butter fat ($\geq$80%) as the oil component thereof but wherein up to about 40 weight % of such butter fat is replaced with the fish oils used in the present invention.

The food regulations of course would require that "butter" made with fish oil be called margarine made with real butter or something else that was not misleading or misdescriptive.

The term "margarine spread" is used to delineate a water-in-oil spread from an oil-in-water spread.

The emulsions of the present invention may be made using technology commonly in use for such purposes, with the exception that the fish oils used in the present invention are blended into the oil phase of such products, prior to the emulsification process, and the deodorization system of the present invention is blended into the water phase of such products, prior to the emulsification process.

The most preferred emulsions of the present invention are those margarine type spreads that have an oil phase content of about 80 to 40 weight % and a milk or aqueous phase content of about 20 to 60 weight %. These spreads would have the following compositions:

|  | Weight % Of The Total Composition | |
|---|---|---|
|  | Broad Range | Preferred Range |
| Oil Phase Component | | |
| liquid non-hydrogenated vegetable oil | 5 to 60 | 20 to 50 |
| partially hydrogenated vegetable oil | 5 to 35 | 10 to 30 |
| lecithin | 0.05 to 0.5 | 0.1 to 0.3 |
| mono- and diglycerides | 0.05 to 0.5 | 0.1 to 0.3 |
| flavor and/or colorant | 0.001 to 0.02 | 0.008 to 0.012 |
| fish oil | 1 to 40 | 5 to 20 |
| Water or Milk Phase Component | | |
| water or aqueous solution at pH of 3 to 9 (preferred pH of 6 to 8) | 10 to 45 | 20 to 35 |
| whey | 0.1 to 3 | 0.5 to 1.5 |
| salt | 0.1 to 4 | 1 to 3 |
| Na benzoate | 0.01 to 0.2 | 0.05 to 0.15 |
| K sorbate | 0.01 to 0.2 | 0.05 to 0.15 |

-continued

| | Weight % Of The Total Composition | |
|---|---|---|
| | Broad Range | Preferred Range |
| | 100 | 100 |

The vegetable oils to be used include corn oil, soybean oil, coconut oil, cottonseed oil, peanut oil, safflower oil, palm kernel oil, sunflower seed oil, palm oil and rapeseed oil.

The emulsifiers include lecithin, glyceryl monostearate, diglycerol monostearate, sorbitol tristearate, sorbitol monostearate and sorbitol monolaurate.

The Deodorization Composition

The fish oil used in the emulsions of the present invention is stabilized against the formation of malodorous aldehydes and alcohols when they are in the oil phase of the products of the present invention by adding to the water phase of such products, prior to the manufacture of such products, a stabilizer system or composition. The stabilizer composition used in this regard is one of (a) aldehyde dehydrogenase plus alcohol dehydrogenase plus nicotinamide adenine dinucleotide (NAD), (b) aldehyde oxidase plus alcohol oxidase plus catalase, and (c) xanthine oxidase plus alcohol oxidase plus catalase.

Each of these (a), (b), and (c) stabilizer systems is used in such amounts as to prevent or retard the formation of malodorous alcohols and/or aldehydes in such fish oils during the shelf life of the emulsions in which the oils are used.

It is believed that these stabilizer systems function in such a way as to transform by oxidation into the corresponding carboxylic acids any malodorous aldehydes or alcohols that may be present or form in the oils during the shelf life of the emulsions. The carboxylic acid derivatives of the offending aldehydes and alcohols are found to be much less volatile and thus much less likely to be a concern as a source of an organoleptically detectible malodor. The acids do not have to be removed during the shelf life of the emulsion.

The amounts of the (a), (b) and (c) stabilizer systems which are to be used in the emulsions of the present invention are not calculated in terms of the composite (a), (b) or (c) systems, but rather in terms of the components of the respective systems. Thus, the various components of the (a), (b), and (c) stabilizer systems are used in the following amounts, which are given in terms of units of activity of the component per gram of the aqueous phase in the emulsion, except for the cofactor NAD which is given in terms of the millimoles concentration of this latter component per gram of the aqueous phase in the emulsion.

Thus stabilizer system (a) uses about 0.01 to 10, and preferably about 0.1 to 1.0, units of aldehyde dehydrogenase, about 0.005 to 5, and preferably about 0.5 to 0.05, units of alcohol dehydrogenase, and about 0.2 to 50, and preferably about 2 to 20, millimoles of NAD.

Stabilizer system (b) uses about 0.01 to 10, and preferably about 0.02 to 1.0, units of aldehyde oxidase, about 0.005 to 5, and preferably about 0.02 to 0.5, units of alcohol oxidase and about 0.1 to 100, and preferably about 0.5 to 2, units of catalase.

Stabilizer system (c) uses about 0.01 to 10, and preferably about 0.1 to 1.0, units of xanthine oxidase, about 0.005 to 5, and preferably about 0.02 to 0.5, units of alcohol oxidase, and about 0.1 to 100, and preferably about 0.5 to 2, units of catalase.

The components of the (a), (b) or (c) systems are also preferably used in the following specific ratios relative to each other:

In stabilizer system (a) the aldehyde dehydrogenase and alcohol dehydrogenase are preferably used in a ratio of units of activity to each other, respectively, of at least 2:1.

In stabilizer system (b) the aldehyde oxidase and alcohol oxidase are preferably used in a ratio of units of activity to each other, respectively, of at least 2:1 and the catalase and aldehyde oxidase are preferably used in a ratio of units of activity to each other, respectively, of at least 2:1.

In stabilizer system (c) the xanthine oxidase and alcohol oxidase are preferably used in a ratio of units of activity to each other, respectively, of at least 2:1 and the catalase and xanthine oxidase are preferably used in a ratio of units of activity to each other, respectively, of at least 2:1.

The Enzymes

The enzymes to be used in the present invention may be obtained from any source thereof.

Food

The food products of the present invention are prepared in emulsified form employing the fish oils to replace some or all of the vegetable oils used heretofore in such products. These products normally contain various amounts of such prior art oils. Although it is technically possible to replace all of the previously used oils (or fats at room temperature) in such products with the fish oils, it appears to be more consumer oriented to only replace a portion of the traditionally used oils with the fish oils. Thus, in food products, in particular, it is preferable, for customer acceptance purposes, to only replace about 1 to 50, and preferably about 5 to 20% of the vegetable or animal oils previously used in such products with the fish oils.

The food grade emulsions are commonly differentiated between those which contain at least 80% oil or fat such as butter, mayonnaise and buttery margarine and those which contain less than 80% oil or fat such as low calorie spreads and salad dressings.

When reformulating these prior art products for the purposes of the present invention, therefore, which commonly use at least 80% by weight of a prior art oil phase and >0 to <20% by weight of a water phase therein, one may replace about 1 to 40, and preferably about 5 to 20%, of such prior art oil phase with the fish oils. Further, when reformulating these prior art products according to the present invention which commonly use less than 80% by weight of a prior art oil phase and ≧20% of a water phase therein, one may replace about 1 to 20, and preferably about 5 to 10%, of such prior art oil phase with the fish oils.

The following Examples are merely illustrative of the scope of the present invention and are not intended as a limitation upon the full scope thereof.

EXAMPLES 1-5

Preparation of 8% Fish Oil Spreads

Five separate spreads were made, each containing 8% fish oil and 30% water with an antioxidant system [2M Glucose and 0.1 mM EDTA (ethylenediamine tetracetic acid, tetra sodium form)]. Control systems, or systems based on the use of the enzyme systems of the present invention, were incorporated into the aqueous phases of the respective products. The resulting spread products were placed in 8-ounce, capped, plastic tubs and stored at 70° F. After 5 days the control and stabilizer systems were evaluated organoleptically by spreading about 3 grams of the respective spread products in a thin film on the bottom of an 8-ounce capped plastic container. The samples were evaluated by personnel trained in lipid and flavor technology.

The five (5) control or stabilizer systems used in this regard were the following:

| System of Example | Description of System |
|---|---|
| 1 | control: no enzymes and no fish oil |
| 2 | control: no enzymes but containing 8% fish oil |
| 3 | Rabbit liver aldehyde oxidase and catalase |
| 4 | Xanthine oxidase, alcohol oxidase and catalase |
| 5 | Aldehyde dehydrogenase, alcohol dehydrogenase and NAD |

All of the spread products contained a milk (aqueous) phase base and an oil phase. The milk base was an aqueous solution at pH 8.0 containing 2M glucose, 0.2M sodium phosphate, 0.1 mM EDTA, 0.1 mM DTT (DL-Dithiothreitol), 2 mM KCl, 14.9 mM potassium sorbate, 21.4 mM sodium benzoate, and 35 mg/ml whey powder. The oil phase contained, on a percent weight per weight basis, 83.28% liquid corn oil, 16.13% partially hydrogenated corn oil, 0.24% lecithin and 0.34% of a mixture of mono and diglycerides. The oil phase base was maintained at 120° F.

System #1 contained 124.0 g of milk base and 309.8 g of oil base.

System #2 contained 140.0 g of milk base, 309.8 g of oil base and 40.0 g fish oil. The fish oil was a non-winterized, refined menhaden oil which contained 250 ppm of citric acid for metal chelation. The fish oil was shipped under nitrogen and stored in a freezer until used.

System #3 was the same as system #2 except for the addition to the milk phase of rabbit liver aldehyde oxidase precipitate (2.9 units) from 200 g of liver, and 10.2 mg of catalase (High Purity Catalase Powder, 114 Baker units/mg, from Finnsugar Biochemicals Inc.).

System #4 was the same as system #2 except for the addition to the milk phase of 100 units of xanthine oxidase from buttermilk (1.5 U/mg protein, 24 mg protein/ml, Grade III, substantially free of uricase, from Sigma Chem. Co.), 1000 units of alcohol oxidase from Pichia pastoris (26 mg protein/ml in a 60% sucrose solution, 27 units/mg protein, from Sigma Chem. Co.) and 10.3 mg catalase.

System #5 was the same as system #2 except for the addition to the milk phase of 450 units of aldehyde dehydrogenase from yeast (potassium-activated powder with 8.9 units/mg solid, from Sigma Chem. Co.), 2716 units of alcohol dehydrogenase from yeast (280 units/mg solid, from Sigma Chem. Co.), and 1.0 g of beta-nicotinamide adenine dinucleotide from yeast (NAD, Grade V-C, 99% contained 3 moles of water/mole of NAD, from Sigma Chem. Co.).

The spreads were prepared by the following procedure. The oil phase, less fish oil, was heated to about 120° F. to liquefy it. The fish oil was briefly heated to about 100° F. to liquefy it, and it was then immediately added to the oil phase and emulsified with the milk phase in a jacketed (−4° C. coolant in jacket) Hobart mixer equipped with a whisk. The emulsions were whipped for about 3-4 minutes until the saturated oil fraction solidified at about 49° F. The solidified emulsions were placed in capped, 8-ounce, plastic tubs, stored at 40° F. for two hours to set and then placed in a 70° F. incubator.

EXAMPLES 6-9

Preparation of Fish Oil Emulsions

Four (4) seventy percent (V/V) fish oil emulsions were prepared by stirring (magnetic stirrer set on highest setting) a milk phase (aqueous phase) into an oil phase at approximately 100° F. in quart Mason jars The jars were capped and slowly stirred at room temperature for about one hour. The samples were stored at room temperature for 18 hours and organoleptically evaluated by trained laboratory personnel. The oil phase in each product (except the control) contained 280 grams of fish oil (described above) with 0.1516 grams of lecithin and 0.2131 grams of a mixture of mono and diglycerides which was heated to about 100° F. to dissolve solids. The milk phase in each product (except the control) consisted of a given enzyme system (see below) and a base aqueous solution of 2M glucose at pH 9.0 containing 0.1 mM EDTA, 100 mM KCl and 40 mM sodium pyrophosphate.

The compositions used in Examples 6-9 were thus as follows:

EXAMPLE 6

Seventy milliliters of oil phase were emulsified with 30 ml of the milk phase base. This was a control sample. It contained no fish oil and no enzymes.

EXAMPLE 7

Seventy milliliters of oil phase were emulsified with 30 ml of milk phase base modified to contain 15 units of aldehyde dehydrogenase activity, 15.4 units of alcohol dehydrogenase activity, and 11 mM NAD (all chemicals described above).

EXAMPLE 8

Seventy milliliters of oil phase were emulsified with 30 ml of milk phase base modified to contain 20 units of alcohol oxidase activity, 18 units of xanthine oxidase activity, and 600 units of catalase activity from bovine liver (from Sigma Chemical Co., 11000 units/mg protein; the alcohol oxidase and xanthine oxidase are described above).

EXAMPLE 9

Seventy milliliters of oil phase were emulsified with 30 ml of milk base modified to contain 3 grams of rabbit liver aldehyde oxidase (which contained 1.5 units of aldehyde oxidase), 20 units of alcohol oxidase activity, and 600 units of catalase activity (alcohol oxidase and catalase were as described above).

Discussion of Example 1 to 5 Tests

The enzymatic removal of fish aroma was examined for these 8% fish oil spreads wherein three different enzyme systems were incorporated into the aqueous phase (30% of the product). The odor reduction by enzymatic treatment relies on the conversion of very volatile aldehydes and alcohols to carboxylic acids which have very low volatility. Two controls were used: Example 1) no enzymes and no fish oil, and Example 2) no enzymes and 8% fish oil. The enzyme treatment of Example 3 consisted of converting aldehydes to carboxylic acids with rabbit liver aldehyde oxidase and catalase to remove the hydrogen peroxide produced by the aldehyde oxidase The enzyme treatment of Example 4 consisted of converting aldehydes to carboxylic acid with xanthine oxidase, converting alcohols to aldehydes with alcohol oxidase, and removing the hydrogen peroxide produced by aldehyde oxidase with catalase The enzyme treatment of Example 5 consisted of converting aldehydes to carboxylic acid with aldehyde dehydrogenase and converting alcohols to aldehydes with alcohol dehydrogenase (both enzymes require the cofactor NAD). The spreads were placed into 8-ounce, capped, plastic tubs, stored at 70° F. for 5 days, and organoleptically evaluated by personnel trained in margarine and flavor technology.

The 8% fish oil spreads were prepared to duplicate a commercial spread with the exception of the deletion of diacetyl which contributes the buttery aroma to such products. The diacetyl was not used in order to simplify the organoleptic aroma evaluation The controls had a strong meaty aroma due to the whey used in the spreads. The control with fish oil also had a very slight fish aroma. All three enzyme treatments removed the meaty aroma and had a slight grassy note. Clearly there was a significant diminution of the whey and fish odors, but with the competitive whey aroma it was difficult to assess the precise degree of odor reduction relative to this fishy odor.

A second attempt at evaluating enzymatic removal of fish oil aroma was done using 70% fish oil emulsions. The enzyme treatments were the same as for the 8% fish oil spreads except for the addition of alcohol oxidase to the rabbit liver aldehyde oxidase system. The emulsions were stored in capped, Mason jars at room temperature for 18 hours before the organoleptic evaluation by the laboratory personnel. The control system had a moderate fish aroma. The aldehyde/alcohol dehydrogenase system showed a significant reduction of fish aroma. Both the xanthine oxidase and aldehyde oxidase based systems showed substantial fish odor reduction, but had a slight ammonia aroma. A different catalase preparation was used in these systems compared to that used in the 8% fish oil spreads which may account for the ammonia aroma However, all three enzyme systems did demonstrate the ability to remove the fishy aroma of fish oil (Table 1 below) and demonstrated the feasibility of this natural approach in controlling fish aroma

TABLE 1

| Enzymatic odor reduction of fish oil systems. | |
|---|---|
| System and Treatment | Relative Strength of Odor |
| Fish oil/margarine of: | |
| Example | |

TABLE 1-continued

| Enzymatic odor reduction of fish oil systems. | |
|---|---|
| System and Treatment | Relative Strength of Odor |
| 1-2  No enzymes | ++++ |
| 3    ALOX + CAT | ++ |
| 4    XOX + AOX + CAT | ++ |
| 5    ALDH + ADH + NAD | ++ |
| Fish oil/emulsion (W/O) of: | |
| Example | |
| 6    No enzymes | ++++ |
| 7    ALDH + ADH + NAD | + |
| 8    XOX + AOX + CAT | ++ |
| 9    ALOX + AOX + CAT | ++ |
| AOX = alcohol oxidase | |
| ALOX = aldehyde oxidase | |
| XOX = xanthine oxidase | |
| ADH = alcohol dehydrogenase | |
| ALDH = aldehyde dehydrogenase | |
| CAT = catalase | |
| ++++ = 100 | |
| ++ = 50 | |
| + = 25 | |

Unless otherwise indicated above, the units of activity of the various enzymes disclosed herein are defined as follows:

(1) One unit of aldehyde dehydrogenase (Lundquist, F., Biochem. J., 68, 172 (1958)) activity will oxidize one micromole of acetaldehyde to acetic acid per minute at 25° C. at pH 8.0 in the presence of beta-nicotinamide adenine dinucleotide, potassium and thiols.

(2) One unit of aldehyde oxidase (Cabre, F. and E. Canela, Biochem. Soc. Transactions, 15, 882 (1987)) activity will oxidize one micromole of $N^1$-methylnicotinamide per minute at 30° C. in 50 mM sodium phosphate at pH 7.8.

(3) One unit of alcohol dehydrogenase (Lamed, R. J. and J. G. Zeikus, Biochem. J., 195, 183 (1981)) activity will convert one micromole of ethanol to acetaldehyde per minute at pH 8.8 at 25° C.

(4) One unit of alcohol oxidase (Janssen, F. W. and H. W. Ruelins, Biochim. Biophys. Acta, 151, 330 (1968)) activity will oxidize one micromole of methanol to formaldehyde per minute at pH 7.5 at 25° C.

(5) One Baker unit of catalase (Scott, D. and F. Hammer, Enzymologia, 22, 194 (1960)) activity will decompose 265 mg hydrogen peroxide under the conditions of assay (25° C., 1.5% $H_2O_2$, pH 7.0, reacted to exhaustion).

(6) One unit of xanthine oxidase (Ackerman, E. and A. S. Brill, Biochim. Biophys. Acta, 56, 390 (1962)) activity will convert one micromole of xanthine to uric acid per minute at pH 7.5 at 25° C.

What is claimed is:

1. A food product comprising a water-in-oil or an oil-in-water emulsion having an oil phase and a water or milk phase wherein said oil phase comprises fish oil and said water or milk phase of said emulsion comprises a stabilizer of
   (a) aldehyde dehydrogenase plus alcohol dehydrogenase plus nicotinamide adenine dinucleotide,
   (b) aldehyde oxidase plus alcohol oxidase plus catalase, or
   (c) xanthine oxidase plus alcohol oxidase plus catalase, wherein said stabilizer is present in such amounts as to prevent or retard the formation of malodorous alcohols and/or aldehydes in such fish oils during the shelf life of said emulsion.

2. A margarine spread as in claim 1 having an oil phase content of 80 to 40 weight % and a water or milk phase content of 20 to 60 weight %.

3. A margarine spread as in claim 2 wherein said (a) stabilizer system is employed.

4. A margarine spread as in claim 2 wherein said (b) stabilizer system is employed.

5. A margarine spread as in claim 2 wherein said (c) stabilizer system is employed.

6. A product of claim 2 comprising the stabilizer system (a) wherein said aldehyde dehydrogenase is present in an amount from about 0.01 to about 10 activity units per gram of water or milk phase, said alcohol oxidase is present in an amount from about 0.005 to about 5.0 activity units per gram of water or milk phase, and said NAD is present in concentrations from about 0.2 to about 50 millimoles per gram of water or milk phase.

7. A product of claim 2 comprising the stabilizer system (b) wherein said aldehyde oxidase is present in an amount from about 0.01 to about 10 activity units per gram of water or milk phase, said alcohol oxidase is present in an amount from about 0.005 to about 5.0 activity units per gram of water or milk phase, and said catalase is present in amounts from about 0.1 to 100 activity units per gram of water or milk phase.

8. A product of claim 2 comprising the stabilizer system (c) wherein said xanthine oxidase is present in an amount from about 0.01 to about 10 activity units per gram of water or milk phase, said alcohol oxidase is present in an amount from about 0.005 to about 5.0 activity units per gram of water or milk phase, said alcohol oxidase is present in an amount from about 0.1 to about 100 activity units per gram of water or milk phase.

9. A product of claim 2 comprising the stabilizer system (a) wherein said aldehyde dehydrogenase and alcohol dehydrogenase are present in a ratio of units of activity to each other of at least 2:1.

10. A product of claim 2 comprising the stabilizer system (b) wherein said aldehyde oxidase and alcohol oxidase are present in a ratio of units of activity to each other of at least 2:1, and said catalase and aldehyde oxidase are present in a ratio of units of activity to each other of at least 2:1.

11. A product of claim 2 comprising the stabilizer system (c) wherein said xanthine oxidase and alcohol oxidase are present in a ratio of units of activity to each other of at least 2:1 and said catalase and xanthine oxidase are present in a ratio of units of activity to each other of at least 2:1.

* * * * *